Figure 1:
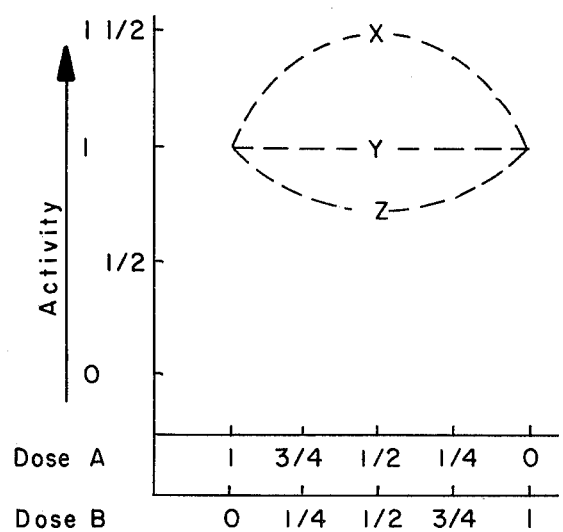

United States Patent [19]

Römer

[11] 4,442,084
[45] Apr. 10, 1984

[54] ANALGESIC AND MYOTONOLYTIC PREPARATIONS

[75] Inventor: Dietmar Römer, Allschwil, Switzerland

[73] Assignee: Sandoz Ltd., Basel, Switzerland

[21] Appl. No.: 407,153

[22] Filed: Aug. 11, 1982

Related U.S. Application Data

[63] Continuation of Ser. No. 296,910, Aug. 27, 1981, abandoned, which is a continuation of Ser. No. 224,086, Jan. 12, 1981, abandoned, which is a continuation-in-part of Ser. No. 138,229, Apr. 7, 1980, abandoned.

[30] Foreign Application Priority Data

Apr. 10, 1979 [CH] Switzerland ............................ 3411/79
Apr. 10, 1979 [CH] Switzerland ............................ 3409/79

[51] Int. Cl.³ .................... A61K 31/425; A61K 3/505
[52] U.S. Cl. ...................................... 424/251; 424/270
[58] Field of Search ........................ 424/319, 251, 270

[56] References Cited

FOREIGN PATENT DOCUMENTS 1248430 10/1971 United Kingdom .
1379677 1/1975 United Kingdom .

OTHER PUBLICATIONS

Cutting et al., B. J. Pharmac. (1975), 54, pp. 171–179.

*Primary Examiner*—Stanley J. Friedman
*Attorney, Agent, or Firm*—Gerald D. Sharkin; Robert S. Honor; Joseph J. Borovian

[57] ABSTRACT

Compositions having enhanced analgesic and myotonolytic activity comprising as active agents (a) an analeptically active quinazolinone and (b) a centrally acting myotonolytic.

19 Claims, 2 Drawing Figures

ANALGESIC AND MYOTONOLYTIC PREPARATIONS

This is a continuation of application Ser. No. 296,910, filed Aug. 27, 1981, now abandoned which in turn is a continuation of application Ser. No. 224,086, filed Jan. 12, 1981, now abandoned, which in turn is a continuation-in-part of Ser. No. 138,229, filed Apr. 7, 1980, now abandoned.

The present invention relates to analgesically and myotonolytically active preparations as well as to methods of inducing analgesia and of treating myotonic conditions.

Various proposals have been made for the combination of analgesic and myotonlytic agents and a number of such preparations for use e.g. in the treatment of pain are available.

In accordance with the present invention it has now surprisingly been found that co-administration of an analgesically active quinazolinone and a centrally acting myotonolytic results in enhanced and advantageous analgesic as well as myotonolytic activity.

More particularly it has been found that co-administration, in particular enteral co-administration, of an analgesically active quinazolinone and a centrally acting myotonolytic unexpectedly provides greater analgesic potency than the sum of the individual components (super-additive synergism). Equally surpisingly it has also been found that enteral administration of an analgesically active quinazolinone will potentiate the activity of an enterally co-administered centrally acting myotonolytic. Moreover, it has been found that e.g. in the dog, enteral co-administration of a quinazolinone and a myotonolytic as aforesaid results in an unexpected and significant raising of the leval of the myotonolytic in the blood plasma (increase in bioavailability) compared with the results obtained on administration of the myotonolytic alone. Enteral administration is to be understood as including, in particular, oral administration.

The co-administration, in particular enteral co-administration, of an analgesically active quinazolinone and a centrally acting myotonolytic, as well as of pharmaceutical preparations containing these components as active agents in combination, is accordingly indicated as being of particular and unforeseen advantage in inducing analgesia, e.g. for the treatment of pain, and also for the treatment of myotonic conditions, e.g. for the treatment of muscle spasm and for muscle relaxation. Such co-administration of said components will accordingly be seen as being of especial potential in the treatment of conditions in which both analgesic and myotonolytic treatment are simultaneously indicated.

In one aspect the present invention therefore provides a pharmaceutical preparation comprising as active agents, (a) an analgesically active quinazolinone and (b) a centrally acting myotonolytic.

It will be appreciated that the analgesic and myotonolytic components employed in accordance with this invention may each be known as possessing other pharmacological activity of greater or lesser degree.

Suitable analgesically active quinazolinones for use in the preparations of the invention are those of formula I,

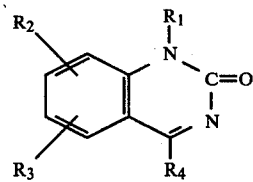

wherein
$R_1$ is $C_{1-5}$ alkyl, $C_{3-6}$ cycloalkyl, $C_{1-4}$ alkyl substituted by $C_{3-6}$ cycloalkyl, $C_{1-5}$ polyhaloalkyl, allyl or propargyl,
either
$R_2$ and $R_3$ are the same or different and each is hydrogen, fluorine, chlorine, bromine, $C_{1-3}$alkyl, -alkylthio or -alkoxy, nitro or trifluoromethyl, with the proviso that one only of $R_2$ and $R_3$ is alkylthio, nitro or trifluoromethyl,
or
$R_2$ and $R_3$ together are 6,7-methylenedioxy, and
$R_4$ signifies a radical of formula Q,

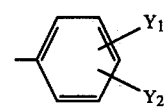

wherein
$Y_1$ and $Y_2$ may be the same or different and each is hydrogen, fluorine, chlorine, bromine, $C_{1-3}$-alkyl or -alkoxy, or trifluoromethyl, with the proviso that one only of $Y_1$ and $Y_2$ is trifluoromethyl.

The compounds of the formula I are in general known e.g. from U.K. Patent Specifications Nos. 1,195,066; 1,248,430; 1,313,789 and 1,379,677, and DOS No. 20 58 722 and have been described as analgesic and anti-inflammatory agents.

In one group of compounds of formula I $R_1$ is $C_{1-5}$-alkyl excluding tertiary alkyl attached to the ring nitrogen atom directly via the tertiary carbon atom or is allyl, propargyl or $C_{3-5}$-cycloalkyl.

Preferred compounds of formula I are those wherein $R_1$ is alkyl, particularly isopropyl,
either
$R_2$ is hydrogen, chlorine, alkyl particularly methyl, or alkoxy particularly methoxy and most preferably is alkyl, especially 7-alkyl
and
$R_3$ is hydrogen,
or
$R_2$ and $R_3$ together are 6,7-methylenedioxy, and $R_4$ is phenyl or halophenyl, especially fluorophenyl and preferably 4-fluorophenyl.

Especially preferred compounds of formula I are:
(1) 1-Isopropyl-4-(4-fluorophenyl)-7-methyl-2(1H)-quinazolinone;
(2) 1-Isopropyl-4-phenyl-7-methyl-2(1H)-quinazolinone;
(3) 1-Isopropyl-4-(4-fluorophenyl)-6,7-methylenedioxy-2(1H)-quinazolinone;
(4) 1-Isopropyl-4-phenyl-6,7-methylenedioxy-2(1H)-quinazolinone;
(5) 1-Cyclopropylmethyl-4-phenyl-6-methoxy-2(1H)-quinazolinone; and (6) 1-(2,2,2-trifluoroethyl)-4-phenyl-6-chloro-2(1H)-quinazolinone, compound (1) being the most preferred.

Suitable centrally acting myotonolytics for use in the preparations of the invention are those of formula II,

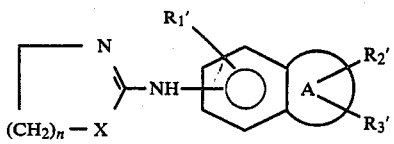

wherein
X is oxygen, sulphur or imino,
n is 1 or 2,
$R_1'$ is hydrogen, halogen, $C_{1-4}$-alkyl, -alkylthio or -alkoxy, trifluoromethyl or hydroxy,
A is a five-membered heterocyclic ring containing at least one heteroatom chosen from nitrogen, oxygen and sulphur and having 2 adjacent carbon atoms common with the benzene ring, with the proviso that the nucleus is other than benzo-2,1,3-thiadiazole, and
$R_2'$ and $R_3'$ are substituents which may be present in ring A, wherein
$R_2'$ is attached to a ring carbon atom and is hydrogen, halogen, $C_{1-4}$-alkyl, -alkoxy or -alkylthio, trifluoromethyl or hydroxy and
$R_3'$ is attached to a ring nitrogen atom and is hydrogen or $C_{1-4}$-alkyl,
with the proviso that when A is [c]pyrrole the nitrogen atom of A is substituted by $C_{1-4}$-alkyl.

The compounds of formula II are in general known, e.g. from DOS No. 2800062, DOS No. 2653005 and DOS No. 2416024. The compounds have been stated to have diverse pharmacological activities, e.g. myotonolytic activity.

In the compounds of formula II, A is, for example, [b] or [c]pyrrole, [d]imidazole, [d]pyrazole, [d]triazole, [b] or [c]furan, [c] or [d]isoxazole, [d]oxazole, [c]furazan, [b] or [c]thiophene, [c] or [d]isothiazole, [d]thiazole, [d](1,2,3)-thiadiazole, [b] or [c]pyrroline, [b] or [c]dihydrofuran or [b]dihydrothiophene. Preferably A is [b]furan, [b]thiophene, [d]oxazole or [d]triazole, especially [b]furan. Halogen means fluorine, chlorine, bromine or iodine, preferably bromine or chlorine. Alkyl, alkoxy or alkylthio preferably contains 2 carbon atoms, especially 1 carbon atom. $R_1'$ is preferably other than hydroxy and is preferably hydrogen, chlorine or methyl. $R_1'$ is preferably ortho to the heterocyclic-amino moiety. $R_2'$ is preferably alkyl, hydrogen or halogen, especially chlorine. The heterocyclic-amino residue is preferably attached to position 4 or 7 of the bicyclic moiety. When the heterocyclic amino moiety is attached to the 4 position of the bicyclic moiety, then $R_2'$, when present, is preferably in the 3 position. $R_2'$, when present, is preferably alkyl. n is preferably 1.

In the compounds of formula II any carbon containing substituent has preferably 1 carbon atom.

A further group of suitable centrally acting myotonolytics comprises those of formula III,

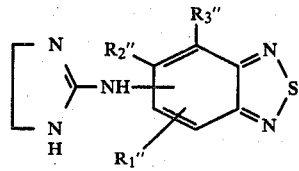

wherein each of $R_1''$, $R_2''$ and $R_3''$, independently, is hydrogen, halogen, $C_{1-4}$-alkyl, -alkoxy or -alkylthio, nitro, cyano or hydroxy.

The compounds of the formula III are also in general known e.g. from Belgian Pat. No. 844532 and DOS 2636309 and have been described as myotonolytics and as anti-tremor and anti-rigor agents.

In the compounds of formula III halogen is preferably fluorine, bromine or chlorine.

Preferred compounds of formula III are those wherein one of the substituents $R_1''$, $R_2''$ and $R_3''$ signifies hydrogen and especially wherein $R_2''$ is hydrogen. Preferably one of the substituents $R_1''$, $R_2''$ and $R_3''$ is other than hydrogen. $R_1''$ is preferably chlorine.

Preferred compounds of formula III are those of formula IIIa,

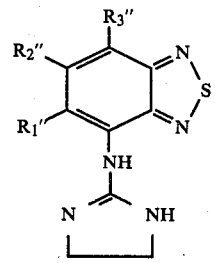

wherein $R_1''$, $R_2''$ and $R_3''$ have the meanings given above.

Especially preferred compounds of the formula IIIa are:
(1) 5-Chloro-4-(2-imidazolin-2-ylamino)-2,1,3-benzothiazole; and
(2) 5-Chloro-7-methyl-4-(2-imidazolin-2-ylamino)-2,1,3-benzothiadiazole.
compound (1) being the most preferred.

A further centrally acting myotonolytic of special use in the preparations of the invention is γ-amino-β-(p-chlorophenyl)-butyric acid, known as baclofen.

The centrally acting myotonolytic, and in particular the compounds of the formula II and III above as well as the compound γ-amino-β-(p-chlorophenyl)-butyric acid may be employed in free base form or in pharmaceutically acceptable salt form e.g. acid addition salt form. Such salt forms are known and include for example the hydrochloride. The activity of any pharmaceutically acceptable salt form will generally be of the same order as that of the respective free base form. As used herein all amounts of such compounds referred to in relation to the compositions of the invention refer to the amount of free base form. Similar considerations apply to weight ratios.

Especially preferred pharmaceutical preparations in accordance with the present invention comprise
(a) as analgesically active quinazolinone-1-isopropyl-4-(4-fluorophenyl)-7-methyl-2(1H)-quinazolinone, and (b) as centrally acting myotonolytic, either 5-chloro-4-(2-imidazolin-2-ylamino)-2,1,3-benzothiadazole, or γ-amino-β-(p-chlorophenyl)-butyric acid.

The preparations according to the invention may be prepared in conventional manner using conventional galenical techniques. For example compositions may be prepared by mixing together of the active agents (a) (analgesically active quinazolinone) and (b) (centrally acting myotonolytic). They may optionally be admixed with conventional pharmaceutical excipients such as fillers, granulating agents, disintegrating agents, binding agents, lubricating agents, dispersing agents, wetting agents, stabilising agents, dyestuffs and preservatives.

The preparations of the invention are suitably put up in solid form e.g. as tablets, powder, granules and capsules or as suspensions or emulsions. Preferably they are put up in unit dosage form particularly in unit dosage form for enteral, especially oral, administration. Such unit dosage forms may contain active agents (a) and (b) separately, e.g. in separate layers in a layer or mantle tablet or in split capsules.

Accordingly, in a further aspect the present invention provides a process for the production of a pharmaceutical preparation which comprises formulating an active agent (a) as stated above with an active agent (b) as stated above and optionally putting up the preparation in unit dosage form.

In yet a further aspect the present invention provides a pack or dispenser-device adapted for the concomitant presentation or administration of an active agent (a) and an active agent (b) as stated above, said active agents being contained in said pack or dispenser-device apart. Conveniently the active agents (a) and (b) are contained in the pack or dispenser-device in separated unit dosage forms. Preferably the pack or dispenser-device bears directions for the concomitant administration of a predetermined amount of active agents (a) and (b). The directions may for example be printed directly on the pack or device.

As already mentioned the combination of (a) an analgesically active quinazolinone and (b) a centrally acting myotonolytic exhibits an enhanced analgesic activity, which is surprisingly more potent than the sum of the activities of the individual components. This effect may be demonstrated in standard tests with animals, e.g. employing the adjuvans arthritis pain test on the rat [A. W. Pircio et al., Europ. J. of Pharmacology 31, 207–215 (1975)], e.g. as follows:

BASIC ANALGESIC TEST METHOD

For the purpose of this test, male OFA rats are employed weighing 160–180 g. The animals are prepared by intra-cutaneous injection of 0.1 ml of a suspension of *Mycobacterium smegmae* (S 1043) in paraffin oil (0.6 mg Mycobact./0.1 ml paraffin oil) into the left hind-paw under ether narcosis. This induces a secondary arthritis of the right hind-paw within the course of the next two or more days. The test for analgesic effectiveness is carried out 16 to 18 days later.

A control measurement is carried out 30 minutes prior to administration of the test-substance, by flexing the ankle-joint of the right hind paw three times and recording the number of vocalisations (pain-reaction). Animals which do not react are eliminated.

Pain-reaction is again determined 1, 3 and 5 hours after oral administration of the test-substance. Animals which exhibit no pain reaction on 2 or 3 of the three flexings are considered to exhibit analgesia. The $ED_{50}$ is determined from the percentage of animals exhibiting analgesia, using probability charts. The confidence limits are determined according to the method of Lichtfield and Wilcoxon. All tests are carried out blind, employing 5 to 15 animals per test substance.

TEST FOR SYNERGISM

In order to establish the presence or absence of synergism the basic analgesic test described above is employed, with analgesia measured three hours after administration of the test substance. Varying proportions of the two test-substance components are used, in fixed dose relationships, based upon the $ED_{50}$ values previously established for the individual components. The degree of activity is then presented graphically. The test components are administered orally in tragacanth suspension and 5 to 15 animals employed per test run. The two test-components are administered in the following dose relationship:

| TEST-RUN | DOSE COMPONENT A | COMPONENT B |
|---|---|---|
| 1 | 1 | 0 |
| 2 | ¾ | ¼ |
| 3 | ½ | ½ |
| 4 | ¼ | ¾ |
| 5 | 0 | 1 |

The presence or absence of synergism for combinations of the test-substance components is determined by graphical representation of the results obtained, in accordance with the principles of Scheler: "Grundlagen der allgemeinen Pharmakologie", Jena, 1969. Thus three basic curves may be obtained as shown diagramatically in FIG. 1 in which a curve x represents potentiation (i.e. super-additive synergism), a curve y represents additive synergism and a curve z represents antagonism.

On oral co-administration of an agent (a) and an agent (b) in accordance with the invention at doses of from 1.6 to 4.9 mg/kg and 2.7 to 0.9 mg/kg respectively, a dose dependent synergism is evidenced in the above test. For the preferred components (a) 1-isopropyl-4-(4-fluorophenyl)-7-methyl-2-(1H)-quinazolinone (component A below) and (b) 5-chloro-4-(2-imidazolin-2-ylamino)-2,1,3-benzothiadiazole (component B below) the following results may for example be obtained:

TEST RESULTS

Determined $ED_{50}$ values (mg/kg p.o.) for the individual components:

| COMPONENT | $ED_{50}$ At ... HOURS AFTER ADMINISTRATION | | |
|---|---|---|---|
| | 1 | 3 | 5 |
| A | ~18 (−45%) | 6.5 | 7.0 |
| B | ~1.8 | 3.6 | ~10 (−60%) |

| | Activity of components in combination: | | | | |
|---|---|---|---|---|---|
| | COMPONENT | | | | |
| | A | | B | | |
| Test-Run | Relative Dosage | mg/kg (p.o.) | Relative Dosage | mg/kg (p.o.) | % activity |
| 1 | 0 | — | 1 | 3.6 | 50 |

-continued

| | Activity of components in combination: COMPONENT | | | | |
|---|---|---|---|---|---|
| | A | | B | | |
| Test-Run | Relative Dosage | mg/kg (p.o.) | Relative Dosage | mg/kg (p.o.) | % activity |
| 2 | ¼ | 1.6 | ¾ | 2.7 | 64 |
| 3 | ½ | 3.2 | ½ | 1.8 | 100 |
| 4 | ¾ | 4.9 | ¼ | 0.9 | 82 |
| 5 | 1 | 6.5 | 0 | — | 50 |

Figure 2:
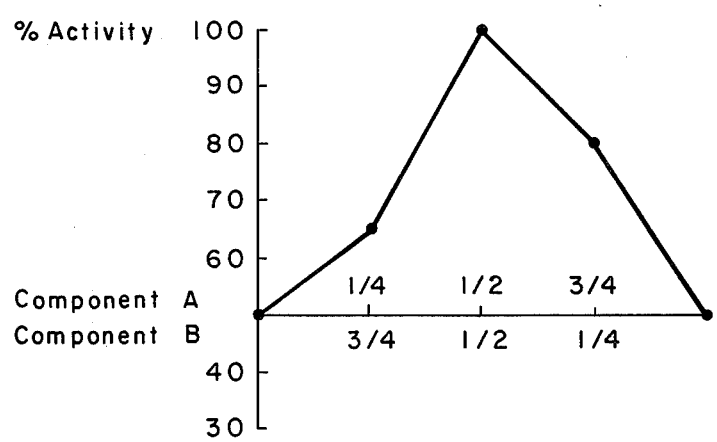

The %-activity obtained in the above test-series was plotted graphically as shown in FIG. 2. The obtained curve clearly indicates super-additive synergistic activity for the components A and B at the tested ratios, in accordance with the principles of Scheler as hereinbefore discussed.

Clinical investigation of the acute analgesic effects of single oral doses also indicates that active agents (a) and (b) when administered in combination have markedly superior activity than the single component alone.

In one such trial unit doses comprising (i) 1 mg of a centrally acting myotonolytic such as 5-chloro-4-(2-imidazolin-2-ylamino)-2,1,3-benzothiadiazole, (ii) 25 mg and (iii) 100 mg of an analgesically active quinazolinone such as 1-isopropyl-4-(4-fluorophenyl)-7-methyl-2(1H)-quinazolinone and (iv) 1 and 25 mg of the myotonolytic and the quinazolinone respectively were administered to 48 otherwise healthy subjects with a history of non-migrainous headache [mostly muscle-contraction (tension) headache: some of combined vascular and tension headache] using a double blind, randomised, partial cross-over design. Subjects with classical migraine, known allergy to drugs, disturbances of the gastro-intestinal tract, cardio-vascular, hepatic and renal system, a history of ulcers or drug dependence and those having ingested analgesics, sedatives or other psychotropic drugs within the previous 4 hours were excluded.

Each subject received two of the four identically appearing test doses (partial cross-over design) and the order of administration was randomised. The subjects were instructed to swallow each dose following the onset of headache of moderate or severe but not mild or unbearable intensity at least 1 hour after meals. The second dose was handed out at least 24 hours after administration of the first.

Each subject was required to classify pain intensity (i) with the aid of a verbal rating and (ii) on a horizontal line (visual analogue scale), 1, 2 and 3 hours after administration of the test dose. Side effects thought to be attributable to the test treatment were also recorded.

Estimation of analgesia based upon analysis of the returns from the trial in accordance with standard techniques indicate that dose (iv) comprising the combination of active agents (a) and (b) was a far more effective medication than doses (i), (ii) or (iii) containing the agents individually. All medications were well tolerated, side effect incidence being very low and randomly distributed among all four doses.

The enhanced myotonolytic activity of active agents (a) and (b) (e.g. 1-isopropyl-4-(4-fluorophenyl)-7-methyl-2(1H)-quinazolinone and 5-chloro-4-(2-imidazolin-2-ylamino)-2,1,3-benzothiadiazole) in combination as compared with the activity of agent (b) alone can also be demonstrated in standard animal tests, for example in the Thalamonal rigor test in the rat, in which the effectiveness of preadministered oral dose in inhibiting rigidity induced by injection of 7.5 mg of Thalamonal is objectively rated by a trained observer employing an Offner-Dynograph. In this test enhancement of activity in dose dependent manner using e.g. doses of 0.25 mg/kg body weight of agent (b) as above in combination with agent (a) at weight ratios of from 1:10 to 1:50 [(b):(a)] is shown for the agents in combination.

The co-administration in particular enteral, e.g. oral co-administration of active agents (a) and (b), is useful in inducing analgesia e.g. in the treatment of inflammatory or painful conditions such as post-operative pain and headache, as well as in the treatment of myotonic conditions, e.g. in the treatment of muscle spasm and for muscle relaxation.

Co-administration of active agents (a) and (b) as aftersaid is especially useful for the treatment of painful conditions associated with muscular spasm and acute painful musculo-skeletal conditions e.g. in the treatment of tension or muscle contraction headache, post-operative pain and of rheumatological conditions.

Accordingly in a yet further aspect of the present invention provides a method of inducing analgesia and/or of treating myotonic conditions in a subject in need of such treatment, which method comprises concomitantly administering to said subject an effective amount of an active agent (a) and an active agent (b) as stated above. Suitably agents (a) and (b) are administered enterally, most preferably orally.

The exact daily dosages of active agents (a) and (b) for use in the method of the invention will of course depend upon the particular analgesically active quinazolinone and centrally acting myotonolytic employed, as well as upon the mode of administration and the condition to be treated.

In general the indicated daily dosage of the analgesic will be of the order of from 40–90% of the standard daily dosage used for inducing analgesia. For the myotonolytic component the daily dosage will be of the order of from 20–90% of the standard daily dosage used in treating myotonic conditions.

A suitable indicated daily dosage is in the range of from about 25 to about 600 mg, and preferably from about 25 to about 400 mg of active agent (a). A preferred daily dosage using the preferred active agent 1-isopropyl-4-(4-fluorophenyl)-7-methyl-2(1H)-quinazolinone is from about 25 to 200 mg.

Conveniently the active agents are administered in sustained release form or alternatively in divided doses 2 to 4 times a day containing e.g. 25, 50, 100 or 200 mg of active agent (a), or in a single dose once a day containing e.g. 25 or 50 mg of active agent (a).

An indicated weight ratio of active agent (a) to active agent (b) is from about 5:1 to about 100:1 preferably from 25:1 to 100:1. For the preferred active agent 1-isopropyl-4-(4-fluorophenyl)-7-methyl-2(1H)-quinazolinone a particularly suitable ratio is from about 10:1, preferably about 20:1 and more preferably about 25:1 to about 50:1. A further suitable ratio is from about 10:1 preferably about 20:1 to about 30:1. The most preferred ratio is about 25:1.

The following Examples are illustrative of compositions for use in the invention.

EXAMPLE 1: Tablet suitable for oral administration

Tablets containing the ingredients indicated below may be prepared by conventional techniques and are useful for oral administration once or twice a day in the treatment of pain and/or muscle spasm.

| Ingredient | Weight (mg) |
| --- | --- |
| 1-isopropyl-4-(4-fluorophenyl)-7-methyl-2(1H)-quinazolinone | 100.00 |
| 5-chloro-4-(2-imidazolin-2-yl-amino)-2,1,3-benzothiadiazole hydrochloride | 2.288 (= 2.0 mg base) |
| Polyoxyethylenepolypropylene-polymer (Pluronic ® F68) | 8.00 |
| Corn Starch | 20.00 |
| Gelatine | 12.00 |
| Cross-linked polyvinylpyrrolidon | 30.00 |
| Lactose | 65.712 |
| Magnesium stearate | 2.00 |
| | 240.000 |

If desired the tablet may be shaped so that it may be easily divided into two.

EXAMPLE 2: Tablet suitable for oral administration

Tablets containing the ingredients indicated below may be prepared by conventional techniques and are useful for oral administration once or twice a day in the treatment of pain and/or muscle spasm.

| Ingredient | Weight (mg) |
| --- | --- |
| 1-isopropyl-4-(4-fluorophenyl)-7-methyl-2(1H)-quinazolinone | 50.00 |
| 5-chloro-4-(2-imidazolin-2-yl-amino)-2,1,3-benzothiadiazole hydrochloride | 2.288 (= 2.0 mg base) |
| Tartaric acid | 2.00 |
| Hydroxypropylcellulose | 1.70 |
| Polyoxyethylenepolypropylene-polymer (Pluronic ® F68) | 4.00 |
| Sodium carboxymethy cellulose | 11.00 |
| Anhydrous lactose | 40.10 |
| Microcrystalline cellulose | 53.012 |
| Magnesium stearate | 0.90 |
| | 165.00 mg |

If desired the tablet may be shaped so that it may be easily divided into two.

EXAMPLE 3: Tablet suitable for oral administration

| Ingredient | Weight (mg) |
| --- | --- |
| Charge A | |
| 1-Isopropyl-4-(4-fluorophenyl)-7-methyl-2(1H)-quinazolinone | 50.0 |
| Hydroxypropylcellulose (Klucel ® LF) | 2.2 |
| Polyoxyethylenepolyoxypropylene-polymer (Pluronic ® F68) | 4.0 |
| Primojel ® | 6.0 |
| Charge B | |
| 5-Chloro-4-(2-imidazolin-2-yl-amino)-2,1,3-benzothiadiazole hydrochloride | 2.288 (= 2.0 mg base) |
| Tartaric acid | 2.0 |
| Anhydrous lactose (200 mesh) | 98.112 |
| Corn Starch | 2.2 |
| Charge C | |
| Corn starch | 2.2 |
| Primojel ® | 5.0 |
| Magnesium stearate | 1.0 |
| | 175.0 mg |

Charges A and B are thoroughly mixed by conventional technique and compounded, again with conventional mixing, with charge C. The combined composition A+B+C is pressed into tablet form of 8 mm diameter suitable for oral administration once or twice daily in the treatment of pain and/or muscle spasm.

EXAMPLE 4: Tablet suitable for oral administration

| Ingredient | Weight (mg) |
| --- | --- |
| Charge A | |
| 1-Isopropyl-4-(4-fluorophenyl)-7-methyl-2(1H)-quinazolinone | 50.0 |
| Hydroxypropylcellulose (Klucel ® LF) | 1.7 |
| Primojel ® | 6.0 |
| Sodium laurylsulfate | 4.0 |
| Charge B | |
| 5-Chloro-4-(2-imidazolin-2-yl-amino)-2,1,3-benzothiadiazole hydrochloride | 2.288 (= 2.0 mg base) |
| Microcrystalline cellulose (Avicel ® PH 102) | 53.012 |
| Tartaric acid | 2.0 |
| Anhydrous lactose | 40.1 |
| Charge C | |
| Primojel ® | 5.0 |
| Magnesium stearate | 0.9 |
| | 165.0 mg |

Charges A and B are thoroughly mixed by conventional technique and compounded, again with conventional mixing, with charge C. The combined composition A+B+C is pressed into tablet form of 8 mm diameter suitable for oral administration once or twice daily in the treatment of pain and/or muscle spasm.

We claim:

1. A pharmaceutical preparation in oral form useful in inducing analgesia and/or in treating myotonolytic conditions comprising: as active agent (a), an analgesically active quinazoline compound selected from the group consisting of 1-isopropyl-4-(4-fluorophenyl)-6,7-methylenedioxy-2(1H)-quinazolinone;

1-isopropyl-4-phenyl-7-methyl-2(1H)-quinazolinone;

1-isopropyl-4-phenyl-6,7-methylenedioxy-2(1H)-quinazolinone;

1-isopropyl-4-(4-fluorophenyl)-7-methyl-2-(1H)-quinazolinone;

1-cyclopropylmethyl-4-phenyl-6-methoxy-2(1H)-quinazolinone; and 1-(2,2,2-trifluoroethyl)-4-phenyl-6-chloro-2(1H)-quinazolinone, and as active agent (b), a centrally acting myotonolytic compound selected from 5-chloro-7-methyl-4-(-imidazolin-2-ylamino)-2,1,3-benzothiadiazole and 5-chloro-4-(2-imidazolin-2-ylamino)-2,1,3-benzothiadiazole, said active agents (a) and (b) being present in the pharmaceutical preparation in a ratio of active agent (a) to active agent (b) of from about 5:1 to about 100:1 parts by weight.

2. A preparation according to claim 1, wherein active agent (a) is 1-isopropyl-4-(4-fluorophenyl)-7-methyl-2(1H)-quinazolinone.

3. A preparation according to claim 1 wherein active agent (a) is 1-isopropyl-4-phenyl-7-methyl-2(1H)-quinazolinone.

4. A preparation according to claim 1 wherein active agent (b) is 5-chloro-4-(2-imidazolin-2-ylamino)-2,1,3-benzothiadiazole.

5. A preparation according to claim 1 wherein active agent (a) is 1-isopropyl-4-(4-fluorophenyl)-7-methyl-2(1H)-quinazolinone and active agent (b) is 5-chloro-4-(2-imidazolin-2-ylamino)-2,1,3-benzothiadiazole.

6. A preparation according to claim 1, wherein the ratio of active agent (a) to active agent (b) is from about 10:1 to about 50:1 parts by weight.

7. A preparation according to claim 6 wherein the ratio is from about 25:1 to about 50:1 parts by weight.

8. A preparation according to claim 7 wherein the ratio is about 25:1 parts by weight.

9. A preparation according to claim 1, in unit dosage form.

10. A preparation according to claim 9 containing from about 25 to 50 mg of active agent (a).

11. A pharmaceutical preparation according to claim 1 wherein active agent (a) is 1-isopropyl-4-phenyl-7-methyl-2(1H)-quinazolinone and active agent (b) is 5-chloro-4-(2-imidazolin-2-ylamino)-2,1,3-benzothiadiazole.

12. A method of inducing analgesia and/or of treating myotonolytic conditions comprising orally administering to a subject in need of such treatment a therapeutically effective amount of a pharmaceutical preparation of claim 1.

13. A method according to claim 12 wherein active agent (a) is 1-isopropyl-4-(4-fluorophenyl)-7-methyl-2(1H)-quinazolin-one.

14. A method according to claim 12 wherein active agent (b) is 5-chloro-4-(2-imidazolin-2-ylamino)-2,1,3-benzothiadiazole.

15. A method according to claim 12 wherein the ratio of active agent (a) to (b) is from about 25:1 to about 50:1 parts by weight.

16. A method according to claim 12 wherein the daily dosage of active agent (a) administered is from 25 to 600 mg.

17. A method according to claim 12 wherein active agent (a) is 1-isopropyl-4-phenyl-7-methyl-2(1H)-quinazolinone.

18. A method according to claim 17 wherein active agent (a) is 1-isopropyl-4-(4-fluorophenyl)-7-methyl-2(1H)-quinazolinone and active agent (b) is 5-chloro-4-(2-imidazolin-2-ylamino)-2,1,3-benzothiadiazole.

19. A method according to claim 11 wherein active agent (a) is 1-isopropyl-4-phenyl-7-methyl-2(1H)-quinazolinone and active agent (b) is 5-chloro-4-(2-imidazolin-2-ylamino)-2,1,3-benzothiadiazole.

* * * * *